United States Patent
Seo et al.

(10) Patent No.: US 11,717,657 B2
(45) Date of Patent: Aug. 8, 2023

(54) DERMAL ADHESIVE PATCH

(71) Applicant: AMOLIFESCIENCE CO., LTD., Seoul (KR)

(72) Inventors: In Yong Seo, Seoul (KR); Ji Hyun Lee, Incheon (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 583 days.

(21) Appl. No.: 16/468,505

(22) PCT Filed: Dec. 8, 2017

(86) PCT No.: PCT/KR2017/014364
§ 371 (c)(1),
(2) Date: Jun. 11, 2019

(87) PCT Pub. No.: WO2018/110907
PCT Pub. Date: Jun. 21, 2018

(65) Prior Publication Data
US 2020/0086099 A1   Mar. 19, 2020

(30) Foreign Application Priority Data

Dec. 12, 2016 (KR) .................. 10-2016-0168638

(51) Int. Cl.
*A61M 35/00* (2006.01)
*A61J 1/06* (2006.01)
*A45D 44/00* (2006.01)

(52) U.S. Cl.
CPC ........... *A61M 35/10* (2019.05); *A45D 44/002* (2013.01); *A61J 1/067* (2013.01)

(58) Field of Classification Search
CPC .... A61K 2300/00; A61K 9/0014; A61K 9/06; A61K 38/00; A61K 9/7084; A61F 13/0276; A61F 13/00029; A61F 13/00063; A61F 13/00987; A61M 35/10; A61M 35/003
See application file for complete search history.

(56) References Cited

U.S. PATENT DOCUMENTS

2007/0225631 A1* 9/2007 Bowlin ................ A61K 38/39
530/356
2010/0125048 A1* 5/2010 Lee ....................... A61Q 19/08
514/18.8

(Continued)

FOREIGN PATENT DOCUMENTS

KR   20090014693 A   2/2009
KR   20130057849 A   6/2013

(Continued)

*Primary Examiner* — Susan S Su
*Assistant Examiner* — Ted Yang
(74) *Attorney, Agent, or Firm* — Rothwell, Figg, Ernst & Manbeck, P.C.

(57) ABSTRACT

A dermal adhesive patch is provided. The dermal adhesive patch is adhered to skin through an ampoule containing a mixing ingredient, a drying ingredient, a viscosity control ingredient, and a moisturizing ingredient. The dermal adhesive patch includes: a support body; and a membrane layer formed as a nanofiber web having pores to block moisture and to allow air to pass through the membrane layer, and detachably laminated on one surface of the support body.

12 Claims, 2 Drawing Sheets

(56) References Cited

U.S. PATENT DOCUMENTS

| | | | | |
|---|---|---|---|---|
| 2010/0191314 | A1* | 7/2010 | Young | A45D 44/002 607/109 |
| 2010/0228204 | A1* | 9/2010 | Beatty | A45D 44/002 604/303 |
| 2010/0324509 | A1* | 12/2010 | Lee | A45D 44/002 604/303 |
| 2011/0045040 | A1* | 2/2011 | Nakamura | A45D 44/002 424/401 |
| 2011/0045041 | A1* | 2/2011 | Golubovic-Liakopoulos | A61P 17/02 514/474 |
| 2011/0300196 | A1* | 12/2011 | Mohammadi | A61K 8/0212 118/712 |
| 2012/0012133 | A1* | 1/2012 | Riscica | A61K 8/14 132/319 |
| 2012/0089103 | A1* | 4/2012 | Tel-Ari | A61M 35/10 604/293 |
| 2012/0192884 | A1* | 8/2012 | Nasu | A45F 5/10 132/319 |
| 2012/0211022 | A1* | 8/2012 | Nakamura | A45D 44/002 132/319 |
| 2012/0308619 | A1* | 12/2012 | Tousley | A45D 44/22 424/401 |
| 2013/0052248 | A1* | 2/2013 | Yuen | A61P 31/04 424/617 |
| 2013/0296761 | A1* | 11/2013 | Goto | A61L 26/0052 602/54 |
| 2013/0345650 | A1* | 12/2013 | Amirouche | A61M 35/10 604/305 |
| 2014/0031770 | A1* | 1/2014 | Lin | A61K 9/703 604/307 |
| 2014/0039422 | A1* | 2/2014 | Scott | A41D 13/1263 604/293 |
| 2014/0052080 | A1* | 2/2014 | Gibson | A61M 35/10 604/293 |
| 2014/0088523 | A1* | 3/2014 | Ottuso | A41B 11/02 604/293 |
| 2014/0121610 | A1* | 5/2014 | Woodley | A61M 35/10 604/290 |
| 2014/0146190 | A1* | 5/2014 | Mohammadi | A61B 5/0077 348/207.2 |
| 2014/0163445 | A1* | 6/2014 | Pallari | A61F 13/122 604/290 |
| 2014/0318565 | A1* | 10/2014 | Ito | A45D 44/22 132/319 |
| 2014/0352031 | A1* | 12/2014 | Choi | A45D 44/002 2/173 |
| 2014/0364365 | A1* | 12/2014 | Wu | A61K 8/0212 514/474 |
| 2015/0125499 | A1* | 5/2015 | Ochiai | B32B 5/26 442/381 |
| 2015/0209561 | A1* | 7/2015 | Everhart | A61M 35/10 604/304 |
| 2015/0265030 | A1* | 9/2015 | Kusukame | A45D 44/002 132/320 |
| 2015/0272855 | A1* | 10/2015 | Kim | A61K 8/922 424/401 |
| 2015/0272906 | A1* | 10/2015 | Jordan | A61M 37/00 604/20 |
| 2015/0335586 | A1* | 11/2015 | Baruzzi | A61J 1/067 424/452 |
| 2016/0089308 | A1* | 3/2016 | Mohammadi | A61K 8/0212 604/20 |
| 2016/0089309 | A1* | 3/2016 | Mohammadi | A61K 8/0212 604/20 |
| 2016/0120766 | A1* | 5/2016 | Lin | A61K 8/733 424/401 |
| 2016/0220444 | A1* | 8/2016 | Brandenburger | B29C 49/46 |
| 2016/0227905 | A1* | 8/2016 | Eisenberg | A45D 44/002 |
| 2017/0340090 | A1* | 11/2017 | Kim | A61K 8/19 |
| 2018/0133658 | A1* | 5/2018 | Seo | B01D 69/148 |
| 2018/0177687 | A1* | 6/2018 | Seo | A45D 44/22 |
| 2018/0186117 | A1* | 7/2018 | Seo | B32B 5/022 |
| 2018/0295971 | A1* | 10/2018 | Seo | A45D 44/22 |
| 2018/0303763 | A1* | 10/2018 | Seo | A61F 13/00017 |
| 2019/0117464 | A1* | 4/2019 | Seo | A61F 13/00063 |

FOREIGN PATENT DOCUMENTS

| KR | 20140091449 A | 7/2014 |
|---|---|---|
| KR | 20160027318 A | 3/2016 |
| KR | 20160059554 A | 5/2016 |

\* cited by examiner

DERMAL ADHESIVE PATCH

CROSS REFERENCE TO RELATED APPLICATION

This application is the national phase entry of International Application No. PCT/KR2017/014364, filed on Dec. 8, 2017, which is based upon and claims priority to Korean Patent Applications 10-2016-0168638, filed on Dec. 12, 2016. The entire contents of which are incorporated herein by reference.

TECHNICAL FIELD

The present invention relates to a dermal adhesive patch, and more specifically, to a dermal adhesive patch which blocks moisture and secures also breathability.

BACKGROUND

Recently, an interest in skin care is steadily increasing. In the past, women who have frequent activities outdoors mainly get skin care, but nowadays, skincare is on the rise, ranging from ordinary housewives to adult men.

As people age, wrinkles form on their faces, and their skin loses elasticity. Particularly, women make great efforts to prevent aging of their skin due to human nature of a pursuit of beauty, and even adult men are increasingly concerned with skin care to invigorate their personal relationships or social life.

Recently, various beauty masks for simplifying skin care are continuously being developed. However, since the conventional beauty masks are manufactured of woven fabric or non-woven fabric, liquid essence runs down due to its weight, and thus the beauty masks are inconvenient to use.

Meanwhile, when skin is injured, a wound is disinfected, medicine such as an ointment is applied thereto, and skin is covered with a medical tape so as to be protected.

However, the conventional medical tape covers medicine that is applied to skin to effectively block the medicine from being exposed to the outside but is not breathable such as to cause skin troubles.

SUMMARY OF THE INVENTION

The present invention is directed to providing a dermal adhesive patch which blocks penetration of effective ingredients therein and secures breathability.

The present invention is directed to providing a dermal adhesive patch which stores a dry-storage material that is difficult to store in a liquid state for a long time and facilitates penetration of a functional component.

One aspect of the present invention provides a dermal adhesive patch, which is attached to skin through an ampoule containing a mixing ingredient, a drying ingredient, a viscosity control ingredient, and a moisturizing ingredient, the patch including a support body and a membrane layer which is formed as a nanofiber web having micropores to block moisture and to allow air to pass through the membrane layer and is detachably laminated on one surface of the support body.

The membrane layer may be a nanofiber web formed to have micropores by electrospinning a spinning solution, in which a synthetic polymer and a solvent are mixed. In this case, an average pore diameter of the micropores may be less than or equal to 10 μm. Accordingly, effects of moisture blocking, breathability, and ultraviolet ray blocking caused by diffuse-reflection can be obtained.

The membrane layer may be attached to a user's skin and may serve as a protective layer that protects the ampoule.

The ampoule may be a mixed solution in which water, alcohol, a polymer, and oil are mixed at a predetermined ratio.

The ampoule may further contain a functional component.

The membrane layer may include a shape-retaining layer, which is laminated on one surface of the support body and formed as a nanofiber web in which nanofibers containing a synthetic polymer are accumulated, and a medicinal solution layer, which is laminated on one surface of the shape-retaining layer and formed as a nanofiber web in which nanofibers containing a functional component and a water-soluble polymer are accumulated.

The functional component may include a dry-storage material which is difficult to store in a liquid state. As one example, the dry-storage material may include any one of a vitamin, an enzyme, a protein, and a peptide-vitamin C derivative.

As another example, the shape-retaining layer may be a nanofiber web which is formed to have micropores by electrospinning a spinning solution, in which a synthetic polymer and a solvent are mixed, and the medicinal solution layer may be a nanofiber web which is formed to have micropores by electrospinning a spinning solution, in which a water-soluble polymer, a functional component, and a solvent are mixed. In this case, the functional component may be a mixture containing at least one of an ingredient for skin whitening, an ingredient for skin wrinkle improvement, an ingredient for ultraviolet ray blocking, an oxidation prevention ingredient, a skin and hair conditioning ingredient, and an antibacterial ingredient. As one example, the functional component may be a mixture containing at least one selected from among a water-soluble collagen, botanical platina, tocopherol, xylitol, and botanical extracts.

The support body may be formed of any one of a non-woven fiber, mesh, silicone, polyethylene terephthalate (PET), polyethylene (PE), polypropylene (PP), and polyurethane (PU). In this case, the support body is removed from the membrane layer when the patch is used.

A release film may be attached to an exposed surface of the membrane layer.

According to the present invention, a membrane layer attached to skin blocks penetration of effective ingredients and secures breathability, and thus an effect of the effective ingredients can be maximized, and a side effect, such as skin troubles, can be prevented.

Further, the membrane layer according to the present invention is formed as a nanofiber web having micropores to refract light that penetrates the micropores, and thus the dermal adhesive patch can obtain an ultraviolet prevention effect without a separate functional component.

Further, the membrane layer according to the present invention is formed as a nanofiber web having micropores to block penetration of fine dust into the skin, and thus the dermal adhesive patch can prevent skin disease that can be caused by fine dust.

A dry-storage material that is difficult to store in a liquid state is contained in the nanofiber web to be stored for a long time and is dissolved by a solvent, and thus the dermal adhesive patch facilitates penetration of functional components into skin.

DETAILED DESCRIPTION OF THE INVENTION

Figure 1:
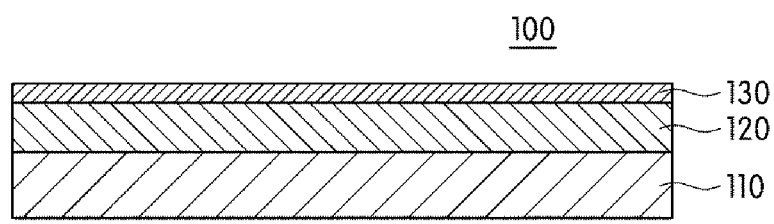
FIG. 1 is a cross-sectional view showing a dermal adhesive patch according to a first embodiment of the present invention.

Hereinafter, embodiments that are easily performed by those skilled in the art will be described in detail with reference to the accompanying drawings. The embodiments of the present invention may be implemented in several different forms, and are not limited to the embodiments described herein. Parts irrelevant to description will be omitted in the drawings to clearly explain the embodiments of the present invention, and the same or similar parts are denoted by same reference numerals throughout this specification.

A dermal adhesive patch 100 or 200 according to one embodiment of the present invention may be attached to a body part to be used with an ampoule disposed therebetween. Accordingly, the dermal adhesive patch 100 or 200 can protect the ampoule applied to a user's skin or facilitate penetration of effective ingredients which are beneficial to the skin into the user's skin.

In this case, the ampoule may be a form of a mixed solution in which a mixing ingredient, a drying ingredient, a viscosity control ingredient, and a moisturizing ingredient are mixed at a predetermined ratio. Specifically, the ampoule may be a form of a mixture in which water, which is the mixing ingredient, alcohol, which is the drying ingredient, a polymer, which is the viscosity control ingredient, and oil, which is the moisturizing ingredient, are appropriately mixed at a predetermined ratio.

That is, the content of the drying ingredient, the viscosity control ingredient, and the moisturizing ingredient of the ampoule may be changed appropriately according to the purpose of use. Accordingly, the entire drying time of the dermal adhesive patch 100 or 200 may vary after the dermal adhesive patch 100 or 200 is attached to the skin. Thus, the dermal adhesive patch 100 or 200 according to one embodiment of the present invention may be implemented in various forms according to the purpose of use, including use while sleeping, use as a mask, use for protection, and the like.

In this case, the ampoule may further contain a functional component besides the above-described four main ingredients. Accordingly, the role and function of the dermal adhesive patch 100 or 200 according to one embodiment of the present invention may vary according to whether the functional component is contained in the ampoule.

As one example, in a case in which the ampoule contains a functional component, since the dermal adhesive patch 100 according to one embodiment of the present invention may be may be attached to the user's skin so as to cover the ampoule, the dermal adhesive patch 100 may serve as a protective layer that makes the functional component contained in the ampoule easily penetrate into the user's skin.

As another example, in a case in which the dermal adhesive patch 200 according to one embodiment of the present invention includes a medicinal solution layer 222 containing a functional component, the dermal adhesive patch 200 may serve as a supply source that supplies a functional component to the user's skin. In this case, because the ampoule does not contain a functional component, the ampoule may serve as a solvent that dissolves the medicinal solution layer 222. Detailed descriptions thereof will be described below.

In the prevent invention, the functional component is an ingredient for skin care and wound treatment and may be a mixture containing at least one of an ingredient for skin whitening, such as arbutin or nicotinamide, ascorbyl glucoside, an ingredient for skin wrinkle improvement, such as retinol or adenosine, an ingredient for ultraviolet ray blocking, such as titanium dioxide, an ingredient for moisturization and skin elasticity, such as snail secretion filtrate, acetyl hexapeptide, red ginseng collagen, aqua ceramide, regenerating peptide, or galactomyces ferment filtrate, a growth factor, such as epithelial growth factor (EGF) or fibroblast growth factor (FGF), proteins for healing, and an antimicrobial component such as silver nano materials, chitosan, and the like.

Further, the functional component may be a mixture containing at least one selected from among water-soluble collagen, botanical platina, tocopherol, xylitol, and botanical extracts.

The above-described dermal adhesive patch 100 or 200 may be formed in a patch form that covers the user's skin.

Figure 2:
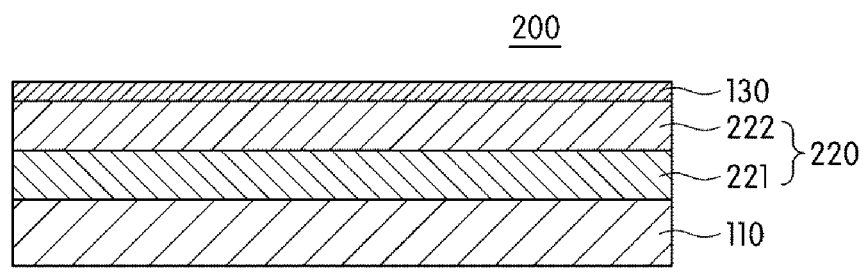
FIG. 2 is a cross-sectional view showing a dermal adhesive patch according to a second embodiment of the present invention.

To this end, as shown in FIGS. 1 and 2, the dermal adhesive patch 100 or 200 according to one embodiment of the present invention may include a support body 110 and at least one membrane layer 120 or 220.

The support body 110 may serve to support the membrane layer 120 or 220 laminated on one surface of the dermal adhesive patch and may be formed in a plate shape having a predetermined area.

As one example, the support body 110 may be formed of non-woven fiber, but the present invention is not limited thereto. In addition to the non-woven fiber, any material that supports the membrane layers 120 and 220, which are formed through electrospinning, such as silicone, polyethylene (PE), polypropylene (PP), polyurethane (PU), and the like, may be used.

Further, the support body 110 may be in a mesh form to support the membrane layer 120 or 220 and implement an exquisite design. In this case, the mesh may be in a form woven of silver, fiber, aluminum wire, and resinous thread.

Meanwhile, the support body 110 may be detachably attached to one surface of the membrane layer 120 or 220 laminated in a vertical direction. That is, when the dermal adhesive patch 100 or 200 according to one embodiment of the present invention is used, the support body 110 supporting the membrane layer 120 or 220 may be detached from the membrane layer 120 or 220. Accordingly, one surface of the membrane layer 120 or 220 in the dermal adhesive patch 100 or 200 may be exposed to the outside.

Therefore, since air may be easily introduced into the user's skin through micropores formed on the membrane layers 120 and 220, skin trouble, such as skin becoming macerated due to air blockage, may be prevented.

As described, the membrane layer 120 or 220 may be laminated on one surface of the support body 110, and one surface of the membrane layer 120 or 220 may be attached to the user's skin with the ampoule disposed therebetween.

Accordingly, the membrane layers 120 and 220 may be formed to block moisture and to secure breathability. As one example, the membrane layer 120 or 220 may be formed as a nanofiber web having micropores to block moisture and to allow air to freely pass therethrough. In this case, an average pore diameter of the micropores may be less than or equal to 10 μm.

Accordingly, as described above, in a case in which the support body 110 is removed during use, and one surface of the membrane layer 120 or 220 is attached to the user's skin with the ampoule disposed therebetween, the dermal adhesive patch 100 or 200 according to one embodiment of the present invention may facilitate penetration of effective ingredients, such as functional components, into skin due to moisture barrier properties of the membrane layers 120 and 220. Further, since the membrane layer 120 or 220 secures breathability, the dermal adhesive patch 100 or 200 according to one embodiment of the present invention may allow air to be easily supplied to skin so as to prevent side effects, such as skin troubles, even when an attached state is maintained for a long time.

Further, since the membrane layer 120 or 220 is formed so that an average pore diameter of the micropores is less than or equal to 10 μm, the membrane layer 120 or 220 may diffuse-reflect light that penetrates the micropores to block ultra-violet (UV) rays without adding separate UV blocking ingredients such as UV blocking ingredients.

In this case, as described above, the membrane layer 120 or 220 may simply serve as a protective layer that cover the user's skin and may serve as a protective layer that cover the user's skin and simultaneously serve to supply effective ingredients to user's skin.

As one specific example, as shown in FIG. 1, the membrane layer 120 of the dermal adhesive patch 100 according to one embodiment of the present invention may be a single layer nanofiber web which is formed to have micropores by electrospinning a spinning solution, in which the synthetic polymer and solvent are mixed. In this case, the solvent may be water or alcohol and may be an organic solvent besides water or alcohol.

In this case, the synthetic polymer may be a fiber-forming polymer that is not dissolved by a solvent and is capable of being electrospun to be formed into a nanofiber web through electrospinning. Accordingly, even when the membrane layer 120 comes into contact with a solvent contained in effective ingredients applied to the user's skin, such as medicine or ampoule, the membrane layer 120 is not dissolved by the solvent and is maintained in a nanofiber web form.

Accordingly, in a state in which the ampoule containing the effective ingredients is applied to the user's skin, when one surface of the membrane layer 120 is attached to cover a body part to which the ampoule is applied and the support body 110 is removed, the membrane layer 120 may protect the ampoule applied to the body part.

Further, in the dermal adhesive patch 100 according to the present embodiment, since the membrane layer 120 contains a synthetic polymer that is not dissolved by a solvent, the membrane layer 120 may be attached to skin for a long time while being maintained in a form of the nanofiber web.

Further, the dermal adhesive patch 100 according to the embodiment of the present invention may allow air to be supplied to a body part, to which the ampoule is applied, of a user from the outside through the micropores formed on the membrane layer 120 and may block effective ingredients contained in the ampoule from being exposed to the outside through the membrane layer 120, and thus the effective ingredients may be effectively absorbed in the body part of the user.

The synthetic polymer may be dissolved by a solvent for the purpose of electrospinning. The synthetic polymer is not particularly limited as long as the synthetic polymer is a resin that may form a nanofiber by electrospinning and that is not dissolved by a solvent. As a non-limiting example, the synthetic polymer may be polyvinylidene fluoride (PVdF), poly (vinylidene fluoride-co-hexafluoropropylene), perfluoropolymer, polyvinyl chloride, polyvinylidene chloride or a copolymer thereof, polyethylene glycol derivative including polyethylene glycol dialkyl ether and polyethylene glycol dialkyl ester, poly (oxymethylene-oligo-oxyethylene), polyoxide including polyethylene oxide and polypropylene oxide, polyvinyl acetate, poly (vinylpyrrolidone-vinyl acetate), polystyrene and polystyrene acrylonitrile copolymer, polyacrylonitrile (PAN), polyacrylonitrile copolymer including polyacrylonitrile methyl methacrylate copolymer, polymethyl methacrylate, polymethyl methacrylate copolymer, or a mixture thereof.

As another example, as shown in FIG. 2, in the dermal adhesive patch 200 according to one embodiment of the present invention, the membrane layer 220 may include a shape-retaining layer 221 and a medicinal solution layer 222, wherein the shape-retaining layer 221 may be formed of a synthetic polymer ingredient that is capable of being electrospun and which may be laminated on one surface of the support body 110, and the medicinal solution layer 222 may be formed of a water-soluble polymer, which is water-soluble and is capable of electrospinning, and a functional component and may be laminated on one surface of the shape-retaining layer 221.

The shape-retaining layer 221 may be a nanofiber web that is formed to have micropores by electrospinning a spinning solution in which a synthetic polymer for electrospinning and a solvent are mixed at an appropriate ratio.

In this case, the synthetic polymer may be a fiber-forming polymer that is not dissolved by a solvent and is capable of being electrospun to be formed into a nanofiber web with micropores through electrospinning. Accordingly, even when the water-soluble medicinal solution layer 222 comes into contact with the ampoule applied to the user's skin to be released into a liquid state or a gel state, the shape-retaining layer 221 is not dissolved by a solvent contained in the ampoule and is maintained in a form of the nanofiber web. Accordingly, the shape-retaining layer 221 may serve to protect the medicinal solution layer 222 released into a liquid state or a gel state.

That is, in the dermal adhesive patch 200 according to one embodiment of the present invention, when the medicinal solution layer 222 is attached to the user's skin with the ampoule disposed therebetween and the support body 110 is removed, the shape-retaining layer 221 may be exposed to the outside. Further, even when the medicinal solution layer 222 is in contact with the solvent and released in a state in which the support body 110 is removed from the membrane layer 220, the dermal adhesive patch 200 according to one embodiment of the present invention may be maintained to be attached to the skin by the shape-retaining layer 221. Further, in a case in which the medicinal solution layer 222 is released by the solvent, the water-soluble polymer ingredient that forms the medicinal solution layer 222 may be absorbed in the shape-retaining layer 221 through the micropores, and thus the shape-retaining layer 221 may serve as a moisturizing layer that maintains moisture.

Thus, the shape-retaining layer 221 of the embodiment of the present invention may not be dissolved by the ampoule to be applied to the user's skin. To this end, the shape-retaining layer 221 may be formed of the same material as the membrane layer 120 described in the above embodiment.

The medicinal solution layer 222 may be a nanofiber web formed to have micropores by electrospinning a spinning solution in which a water-soluble polymer, a functional component, and a solvent are mixed at an appropriate ratio.

That is, since the medicinal solution layer 222 may be formed of the spinning solution in which the water-soluble polymer and the functional component are mixed, the medicinal solution layer 222 may be changed to a release state when coming into contact with the ampoule applied to the user's skin. Accordingly, the functional component contained in the medicinal solution layer 222 may be absorbed in the skin, and the water-soluble polymer contained in the medicinal solution layer 222 may be absorbed in the shape-retaining layer 221.

In this case, the water-soluble polymer ingredient is not particularly limited as long as the water-soluble polymer ingredient is a polymer ingredient that is dissolved in water or alcohol and forms a nanofiber through electrospinning. As a non-limiting example, the water-soluble polymer ingredient may be a mixture that contains at least one selected from among polyvinyl alcohol (PVA), polyvinyl pyrrolidone (PVP), polyethylene oxide (PEO), carboxyl methyl cellulose (CMC), starch, polyacrylic acid (PAA), and hyaluronic acid.

Further, in the embodiment, the ampoule may contain a functional component, but when the medicinal solution layer 222 contains the functional component, the ampoule may not contain a functional component.

Meanwhile, the functional component contained in the medicinal solution layer 222 may be a dry-storage material that is difficult to store in a liquid state. When the water-soluble polymer is dissolved, the dry-storage material may be released into a liquid or gel state to be easily absorbed in the user's skin.

As one example, the dry-storage material may be a vitamin, enzyme, protein, peptide-vitamin C derivative, and the like. Generally, the above-described dry-storage materials have a property of being decomposed only in liquid. However, the dry-storage material is difficult to store in a liquid state for a long time.

In the present invention, the dry-storage material that is difficult to store in a liquid state is contained in a spinning solution with the water-soluble polymer ingredient and the solvent, and a nanofiber is formed of the spinning solution containing the dry-storage material through electrospinning, and thus the medicinal solution layer 222 may be formed in a nanofiber web form. Accordingly, the dry-storage material may be contained in the nanofiber that forms the medicinal solution layer 222 in a dry state.

Accordingly, the dermal adhesive patch 200 according to one embodiment of the present invention may store a dry-storage material that is difficult to store in a liquid state for a long time, and in a case in which a water-soluble polymer is dissolved by a solvent, a dry functional component may be released with the water-soluble polymer and may be transferred to skin so as to easily penetrate skin.

That is, when the dermal adhesive patch 200 according to one embodiment of the present invention is attached to skin, the water-soluble polymer that forms the medicinal solution layer 222 may be dissolved by a solvent, and the functional component contained in the water-soluble polymer may be released. Accordingly, the released functional component may be absorbed in skin, and the water-soluble polymer dissolved by a solvent may be absorbed in the shape-retaining layer 221.

Meanwhile, a predetermined percentage of oil may be contained in a spinning solution that forms the medicinal solution layer 222 so that a time duration for which the medicinal solution layer 222 is dissolved when coming into contact with a solvent is adjusted appropriately. An entire dry time of the membrane layer 220 attached to the user's skin may be changed after the membrane layer 220 is attached to the user's skin. Accordingly, the dermal adhesive patch 200 according to one embodiment of the present invention may be formed in various forms according to the purpose of use, including use while sleeping, use as a mask, use for protection, and the like, and may be set to have a dry time appropriate for the purpose of use.

In the dermal adhesive patch 100 or 200 according to one embodiment of the present invention, a release film 130 may be laminated on one surface of the membrane layer 120 or 220 to prevent the membrane layer 120 or 220 from being exposed to the outside. As one example, the release film 130 may be a fluorine polymer resin, such as polyethylene terephthalate (PET), polypropylene (PP), polyethylene (PE), or a release paper.

The above-described dermal adhesive patch 100 or 200 may be attached to the user's skin so as to increase physiological function of skin and to supply nutrition for stimulating metabolism. Accordingly, the above-described dermal adhesive patch 100 or 200 may be used as a beauty sheet, such as a mask pack for keeping skin beautiful, healthy, and elastic (see FIG. 3A) or may be used as a protective sheet for protecting a wound (see FIGS. 3B and 3C).

Figure 3A:
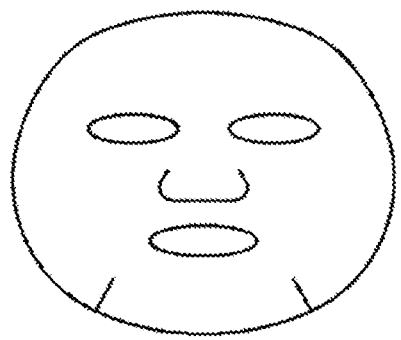
FIGS. 3A, 3B, and 3C are views showing various forms of a dermal adhesive patch according to one embodiment of the present invention.
Figure 3B:
Figure 3C:

That is, as shown in FIGS. 3A-3C, the dermal adhesive patch 100 or 200 according to one embodiment of the present invention may be manufactured in a form appropriate for a body structure through an appropriate process including cutting, incising, punching, folding, and the like. As one example, the dermal adhesive patch 100 or 200 may have a size and a shape that may be attached to any body part such as a face, a neck, hands, ears, legs, belly, arms, shoulders, or the like.

Meanwhile, although the dermal adhesive patch 200 according to one embodiment of the present invention has been described with a functional component only being contained in the medicinal solution layer 222 in a case in which the membrane layer 120 includes the shape retaining layer 221 and the medicinal solution layer 222, the present invention is not limited thereto. The functional component may even be contained in the shape-retaining layer 221. That is, the shape-retaining layer 221 may further contain a functional component in a spinning solution thereof in addition to a solvent and a synthetic polymer ingredient for maintaining a nanofiber web form.

Further, a spinning method for forming the membrane layer 120 or 220 in a form of a nanofiber web according to the present invention may include any one of general electrospinning, air electrospinning, electrospinning, electrospraying, centrifugal electrospinning, and flash electrospinning.

Although the above embodiments of the present invention have been described, the scope of the present invention is not limited to the embodiments described in the specification. Those skilled in the art who understand the spirit of the present invention may easily accomplish other embodiments by the addition, modification, and removal of components within the same spirit, but those are to be construed as being included in the spirit of the present invention.

The invention claimed is:

1. A dermal adhesive patch that is configured to be attached to skin to which an ampoule containing a mixing ingredient, a drying ingredient, a viscosity control ingredient, and a moisturizing ingredient is applied, the patch comprising:
   a support body; and
   a membrane layer formed as a nanofiber web having micropores with an average pore diameter of 10 µm or less and configured to block moisture and to allow air to pass through the membrane layer, wherein the membrane layer is detachably laminated on one surface of the support body,
   wherein the membrane layer is configured to be attached to a user's skin in a state in which the support body is removed,
   wherein the membrane layer includes a shape-retaining layer and a medicinal solution layer,
   wherein the shape-retaining layer is laminated on the one surface of the support body and is formed as a first nanofiber web which is formed to have micropores by electrospinning a first spinning solution, in which a synthetic polymer which is a fiber-forming polymer that is not dissolved by a first solvent contained in the ampoule and a second solvent are mixed,
   wherein the medicinal solution layer which is laminated on one surface of the shape-retaining layer and is formed as a second nanofiber web which is formed to have micropores by electrospinning a second spinning solution, in which a functional component, a water-soluble polymer and a third solvent are mixed so as to be released by the first solvent contained in the ampoule, and
   wherein the shape-retaining layer having the synthetic polymer which is a fiber-forming polymer is not dissolved by the first solvent contained in the ampoule and maintains the form of the first nanofiber web having micropores, and
   wherein the shape-retaining layer is a protective layer configured to protect the medicinal solution layer released by the first solvent contained in the ampoule while being maintained in the nanofiber web form having micropores.

2. The dermal adhesive patch of claim 1, wherein the ampoule is a mixed solution in which water, alcohol, a polymer, and oil are mixed at a predetermined ratio.

3. The dermal adhesive patch of claim 1, wherein the ampoule further contains an ampoule functional component.

4. The dermal adhesive patch of claim 1, wherein the functional component includes a dry-storage material which is difficult to store in a liquid state.

5. The dermal adhesive patch of claim 4, wherein the dry-storage material includes any one of a vitamin, an enzyme, a protein, and a peptide-vitamin C derivative.

6. The dermal adhesive patch of claim 3, wherein the ampoule functional component is a mixture containing at least one of an ingredient for skin whitening, an ingredient for skin wrinkle improvement, an ingredient for ultraviolet ray blocking, an ingredient for oxidation prevention, an ingredient for skin and hair conditioning, and an antibacterial ingredient.

7. The dermal adhesive patch of claim 6, wherein the ampoule functional component is a mixture containing at least one selected from among a water-soluble collagen, botanical platina, tocopherol, xylitol, and botanical extracts.

8. The dermal adhesive patch of claim 1, wherein the support body is formed of any one of a non-woven fiber, mesh, silicone, polyethylene terephthalate (PET), polyethylene (PE), polypropylene (PP), and polyurethane (PU).

9. The dermal adhesive patch of claim 1, wherein a release film is attached to an exposed surface of the membrane layer.

10. The dermal adhesive patch of claim 1, wherein the functional component is a mixture containing at least one of an ingredient for skin whitening, an ingredient for skin wrinkle improvement, an ingredient for ultraviolet ray blocking, an ingredient for oxidation prevention, an ingredient for skin and hair conditioning, and an antibacterial ingredient.

11. The dermal adhesive patch of claim 10, wherein the functional component is a mixture containing at least one selected from among a water-soluble collagen, botanical platina, tocopherol, xylitol, and botanical extracts.

12. The dermal adhesive patch of claim 1, wherein the synthetic polymer is polyvinylidene fluoride (PVDF), poly (vinylidene fluoride-co-hexafluoropropylene), perfluoropolymer, polyvinyl chloride, polyvinylidene chloride, polyethylene glycol dialkyl ether, polyethylene glycol dialkyl ester, poly (oxymethylene-oligo-oxyethylene), polyoxide including polyethylene oxide and polypropylene oxide, polyvinyl acetate, poly (vinyl pyrrolidone-vinyl acetate), polystyrene and polystyrene acrylonitrile copolymer, polyacrylonitrile (PAN), polyacrylonitrile methyl methacrylate copolymer, polymethyl methacrylate, polymethyl methacrylate copolymer, or a mixture thereof.

* * * * *